United States Patent [19]

Engel

[11] 4,235,927

[45] Nov. 25, 1980

[54] INSECTICIDAL BENZYLFURYLMETHYL PERHALOALKYLVINYLCYCLO-PROPANECARBOXYLATES

[75] Inventor: John F. Engel, Medina, N.Y.

[73] Assignee: FMC Corporation, Philadelphia, Pa.

[21] Appl. No.: 55,212

[22] Filed: Jul. 6, 1979

Related U.S. Application Data

[63] Continuation-in-part of Ser. No. 12,266, Feb. 15, 1979, abandoned, Ser. No. 927,198, Jul. 24, 1978, abandoned, and Ser. No. 870,973, Jan. 20, 1978, abandoned.

[51] Int. Cl.³ .................. A01N 9/28; C07D 307/54
[52] U.S. Cl. .................. 424/285; 260/347.4; 260/544 L; 560/124; 562/506
[58] Field of Search .................. 260/347.4; 424/285

[56] References Cited

U.S. PATENT DOCUMENTS

| | | | |
|---|---|---|---|
| 4,024,163 | 5/1977 | Elliott et al. | 260/347.4 |
| 4,157,447 | 6/1979 | Engel | 560/8 |
| 4,183,948 | 1/1980 | Huff | 424/304 |

FOREIGN PATENT DOCUMENTS

| | | |
|---|---|---|
| 858137 | 2/1978 | Belgium . |
| 863151 | 7/1978 | Belgium . |
| 52-14749 | 2/1977 | Japan . |

*Primary Examiner*—Richard Raymond
*Attorney, Agent, or Firm*—Robert L. Andersen; Robert M. Kennedy; H. Robinson Ertelt

[57] ABSTRACT

Perhaloalkylvinylcyclopropanecarboxylates having the general formula

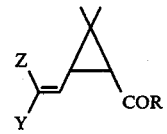

I are disclosed wherein one of Y and Z is a perhaloalkyl group and the other is hydrogen, halogen, or lower alkyl. Compounds in which R is hydroxy, halogen or lower alkoxy are intermediates for preparation of insecticidal esters in which R is an optionally substituted benzylfurylmethoxy group. The insecticidal efficacy and preparation of the compounds and intermediates therefor are described and exemplified.

9 Claims, No Drawings

INSECTICIDAL BENZYLFURYLMETHYL PERHALOALKYLVINYLCYCLOPROPANECARBOXYLATES

This application is a continuation in part of copending applications Ser. Nos. 012,266 filed Feb. 15, 1979, 927,198 filed July 24, 1978 and 870,973, filed Jan. 20, 1978, all now abandoned.

The present invention is directed to a novel class of cyclopropanecarboxylate insecticides, and to an insecticidal method and composition. More particularly, the invention is directed to insecticidal benzylfurylmethyl perhaloalkylvinylcyclopropanecarboxylates.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. A noteworthy advance in this area was the discovery by Elliott et al. of certain highly active dihalovinylcyclopropanecarboxylates such as permethrin, the common name for 3-phenoxybenzyl 3-($\beta,\beta$-dichlorovinyl)-2,2-dimethylcyclopropanecarboxylate. This class of compounds is set forth in U.S. Pat. No. 4,024,163, issued May 17, 1977.

The present invention provides a new class of insecticidal cyclopropanecarboxylates, namely, benzylfurylmethyl perhaloalkylvinylcyclopropanecarboxylates, exhibiting a remarkable level of insecticidal activity. The present invention also provides novel insecticidal compositions of the foregoing compounds, and a method for controlling insects.

In this application, the term "lower", as applied to an alkyl group means having 1–6 carbon atoms, preferably 1–4 carbon atoms. The term "halo" or "halogen" means bromine, chlorine, or fluorine. With respect to a perhaloalkyl group the halogens may be the same or different and are suitably selected from fluorine and chlorine with fluorine being preferred. These definitions are applicable throughout the specification and claims except where a contrary meaning is clearly indicated.

The insecticidal compounds of this invention are cyclopropanecarboxylates of the general formula

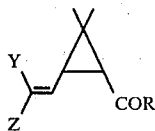

wherein one of Y and Z is a perhaloalkyl group having 1 to 4 carbon atoms, preferably 1 or 2 carbon atoms, and the other is hydrogen, halogen, or lower alkyl. Particularly desirable compounds are cyclopropanecarboxylates of formula I in which one of Y and Z is trihalomethyl, preferably trifluoromethyl, and the other is halogen. R is —OR$^1$, where R$^1$ is represented by the formula

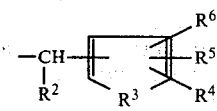

in which R$^2$ is hydrogen, lower alkyl, ethynyl, cyano, or trihalomethyl; R$^3$ is divalent oxygen; R$^4$ is benzyl which may be ring substituted with one to three substituents selected from halogen and lower alkyl; R$^5$ and R$^6$ are independently hydrogen, lower alkyl or halogen, lower alkenyl, phenyl, phenoxy, benzyl, or phenylthio, advantageously, hydrogen, lower alkyl or halogen.

The preferred compounds of this invention are those in which R$^1$ is represented by the formula

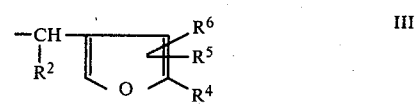

in which R$^2$, R$^5$ and R$^6$ are each hydrogen and R$^4$ is as previously defined.

The insecticidal compounds of this invention and certain intermediates therefor exist as cis and trans geometrical isomers, i.e., the carboxy and the substituted vinyl groups at the 1 and 3 positions of the cyclopropane ring are either cis and trans with respect to each other. Preparation of such compounds will usually yield a mixture of cis and trans isomers, designated cis,trans, in which the ratio of cis to trans may vary over a wide range. For purposes of this application the designations cis and trans are assigned in accordance with P. E. Burt, et al., *Pestic Sci.*, 5 791-799 (1974). The compounds of this invention may also exist as E or Z isomers or as mixtures of E and Z isomers, designated E,Z, depending on the spatial relationship of substituents on the $\alpha$-carbon of the vinyl group to those on the $\beta$-group of the vinyl group.

In the cyclopropanecarboxylate art it is known there may be substantial differences in the level of insecticidal activity between the cis and trans isomers. In general, as between the cis and trans isomer of a given cyclopropanecarboxylate, the cis isomer is usually more active than the trans and also more active than the cis,-trans mixture. Similar differences in activity may also occur with respect to the E and Z isomers.

Unless a contrary intent is expressed, the invention embodies and includes all compounds in which the carboxy and substituted vinyl groups at the 1 and 3 positions of the cyclopropane ring are cis or trans, or a mixture of cis and trans configuration with respect to each other. Similarly, while the invention is illustrated with a mixture of the E and Z isomers, the individual isomers, as well as the mixtures, are also contemplated by and within the scope of the present invention. The enantiomers of these isomers are also included within the scope of the invention.

The compounds may be prepared from alkanoates of the formula

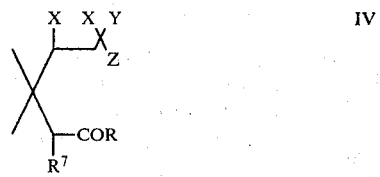

in which Y and Z are defined as above; R is lower alkoxy, such as methoxy or ethoxy, or an alcohol residue of Formula II or III; R$^7$ is hydrogen, lower alkylcarbonyl, lower alkoxycarbonyl, or cyano, preferably hydrogen; and X is chloro or bromo. Example 1 illustrates a method for preparation of the alkanoate intermediates of Formula IV whereby a lower alkyl 3,3-dimethyl-4-pentenoate is allowed to react with a compound of the formula $X_2C(Y)(Z)$ wherein X, Y, and Z are as defined above.

Dehydrohalogenation of the compound of formula IV followed, if necessary, by hydrolysis of the ester and, also if necessary, halogenation of the resulting carboxyl group gives a compound of the formula

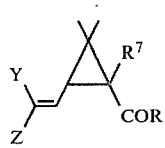

V in which R is lower alkoxy, hydroxy, halogen, or an alcohol residue such as 5-benzyl-3-furylmethoxy, and Y, Z and $R^7$ are as defined above. The dehydrohalogenation reaction may proceed through one or more intermediates of the formulas:

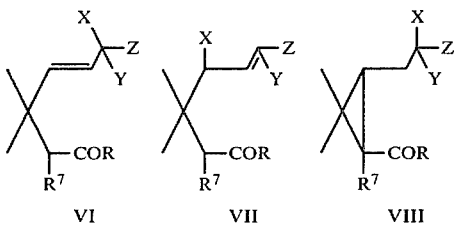

and may be conducted in a single step by removal of 2 halogens to give a compound of formula V directly or in multiple steps under conditions allowing a sequential removal of the halogens in separate reactions. These intermediates or mixtures thereof may be recovered if desired. The compound of formula V is then converted to the compound of formula I by methods known to the art, for example, by removing $R^7$ (if other than hydrogen) and, where R is lower alkoxy, hydroxy, or halogen, esterifying or transesterifying with an alcohol residue of formula II or III.

The examples which follow illustrate preparation of the insecticidal compounds and novel intermediates therefor in accordance with the general method described above. In the examples all temperatures are in degrees centigrade, all pressures are in mm. Hg, and reduced pressure for concentrations of liquid was produced by a water aspirator unless otherwise specified.

Example 1 illustrates the preparation of compounds of formula IV.

EXAMPLE 1

SYNTHESIS OF ETHYL 3,3-DIMETHYL-4,6,6-TRICHLORO-7,7,7-TRIFLUOROHEPTANOATE

A stirred solution of 44.6 g (0.267 mole) of ethyl 3,3-dimethyl-4-pentenoate, 100 g (0.533 mole) of 1,1,1-trichlorotrifluoroethane, 0.27 g (0.0027 mole) of cuprous chloride, and 8.2 g (0.134 mole) of ethanolamine in 270 ml of tertiary butyl alcohol, under a nitrogen atmosphere, was heated at reflux for 16 hours. The reaction mixture was cooled to ambient temperature and extracted with three portions of 100 ml each of diethyl ether. A precipitate formed in the extracts, and was removed by vacuum filtration. The filter cake was washed with two portions of 25 ml each of diethyl ether. The ether extracts were combined with the washings, and the whole was concentrated under reduced pressure to an oily residue. Remaining volatile components were removed from the residue under further reduced pressure using a vacuum pump. The residue was subjected to distillation under reduced pressure to give 78.3 g of ethyl 3,3-dimethyl-4,6,6-trichloro-7,7,7-trifluoroheptanoate; bp 85°–87° at 0.12–0.15 mm. The nmr spectrum was consistent with the assigned structure.

Additional intermediates of formula IV, prepared in accordance with the method illustrated in Example 1, are set forth in Table I.

Examples 2 and 3 illustrate preparation of the lower alkyl esters of formula V. Example 2 is a two-step process via the intermediate of formula VIII. Example 3 is a one-step process.

EXAMPLE 2

SYNTHESIS OF METHYL CIS,TRANS-3-[2-CHLORO-3,3,3-TRIFLUOROPROPENYL]-2,2-DIMETHYLCYCLOPROPANECARBOXYLATE

A. Preparation of methyl cis,trans-3-[2,2-dichloro-3,3,3-trifluoropropyl]-2,2-dimethylcyclopropanecarboxylate as an intermediate A stirred solution of 37.0 grams (0.112 mole) of methyl 3,3-dimethyl-4,6,6-trichloro-7,7,7-trifluoroheptanoate, 50 ml of tert-butyl alcohol, 50 ml of dimethylformamide, and 50 ml of hexane, under an argon atmosphere, was cooled to −5° C. To the stirred solution was added dropwise a solution of 16.4 grams (0.14 mole) of potassium tert-butoxide in 200 ml of tert-butyl alcohol at such a rate so as to maintain the reaction mixture temperature at −3° to −5° C. Upon complete addition, the reaction mixture was stirred for 4 hours at −3° to −5° C., then poured into a solution of 8.0 grams of ammonium chloride in 250 ml of water. The mixture was extracted with two portions of 200 ml each of diethyl ether. The combined ether extracts were washed with two portions of 200 ml each of water. The ether layer was dried with sodium sulfate and filtered. The filtrate was evaporated under reduced pressure to a residual oil. The oil was distilled under reduced pressure to give 19.8 grams of methyl cis,trans-3-[2,2-dichloro-3,3,3-trifluoropropyl]-2,2-dimethylcyclopropanecarboxylate; b.p. 55°–57° C./0.09 mm Hg. The ir and the nmr spectra were consistent with the proposed structure.

Elemental analysis calc'd for $C_{10}H_{13}Cl_2F_3O_2$: C 40.98; H 4.47. Found: C 41.50; H 4.41.

B. Synthesis of methyl cis,trans-3-[2-chloro-3,3,3-trifluoropropenyl]-2,2-dimethylcyclopropanecarboxylate A stirred solution of 30.6 g (0.105 mole) of methyl cis,trans-3-[2,2-dichloro-3,3,3-trifluoropropyl]-2,2-dimethylcyclopropanecarboxylate and 17.6 g (0.116 mole) of 1,5-diazabicyclo[5.4.0]undec-5-ene in 100 ml of dimethylformamide was heated at 100° C. for 4 hours. The reaction mixture was cooled and poured into a solution of 37.2 ml of concentrated hydrochloric acid in 300 ml of water. The mixture was extracted with three portions of 200 ml each of diethyl ether. The combined ether extracts were washed with an aqueous saturated solution of sodium chloride. The ether layer was dried with sodium sulfate and filtered. The filtrate was evaporated under reduced pressure to give a residual oil. The oil was dissolved in hexane, treated with decolorizing carbon, and filtered. The filtrate was evaporated under reduced pressure to a residual oil. The oil was distilled under reduced pressure to give in three fractions 10.0 grams of methyl cis,trans 3-[2-chloro-3,3,3-trifluoropropenyl]-2,2-dimethylcyclopropanecarboxylate; b.p. 40°-60° C./0.05 mm. The ir and the nmr spectra were consistent with the proposed structure. The nmr spectra indicated an 88:12 mixture of cis:trans isomers.

Analysis calc'd for $C_{10}H_{12}ClF_3O_2$: C 46.80; H 4.71; Found: C 46.91; H 4.79.

EXAMPLE 3

SYNTHESIS OF ETHYL CIS,TRANS-3-[2-CHLORO-3,3,3-TRIFLUORO-PROPENYL]-2,2-DIMETHYLCYCLO-PROPANECARBOXYLATE

To a stirred solution of 78.3 g (0.228 mole) of ethyl 3,3-dimethyl-4,6,6-trichloro-7,7,7-trifluoroheptanoate in 200 ml of distilled ethanol was added dropwise at ambient temperature 500 ml of an ethanolic solution of sodium ethoxide prepared from 11.5 g of metallic sodium (0.50 mole). After complete addition, the reaction mixture was stirred for one hour at ambient temperature, then allowed to stand for 18 hours. The cloudy reaction mixture was filtered and the filtrate evaporated under reduced pressure to give a residue. The residue was slurried in 200 ml of water, and the mixture was extracted with three portions of 50 ml each of diethyl ether. The combined extracts were dried with sodium sulfate and filtered. The filtrate was evaporated under reduced pressure to give, as a residual oil, 58.5 g of ethyl cis,trans-3-[2-chloro-3,3,3-trifluoropropenyl]-2,2-dimethylcyclopropanecarboxylate. The nmr and the ir spectra were consistent with the assigned structure and indicated the product was a mixture of approximately equal parts of cis and trans isomers.

Additional intermediates of formula VIII, prepared in accordance with the method illustrated in Example 2A, are set forth in Table II.

Additional lower alkyl esters of formula V, prepared in accordance with Example 2 or Example 3 above, are set forth as Compounds 3.1 to 3.8 of Table III. Compounds 3.1 through 3.7 were prepared in accordance with Example 2. Compound 3.8 was prepared in accordance with Example 3.

EXAMPLE 4

SYNTHESIS OF TRANS AND CIS,TRANS-3-[2-CHLORO-3,3,3-TRIFLUORO-PROPENYL]-2,2-DIMETHYLCYCLO-PROPANECARBOXYLIC ACID

A solution of 16.2 g (0.06 mole) of ethyl cis,trans-3-[2-chloro-3,3,3-trifluoropropenyl]-2,2-dimethylcyclopropanecarboxylate in 94 ml (0.078 mole) of a stock solution containing 3.34 g of sodium hydroxide, 94 ml of ethanol and 6 ml of water was stirred while heating under reflux for a period of 18 hours. The reaction mixture was concentrated under reduced pressure, 25 ml of water was added, and the mixture was acidified to pH 1 using 6 N hydrochloric acid. The acidified mixture was extracted with two portions of 50 ml each of diethyl ether. The combined extracts were dried with magnesium sulfate and filtered. The filtrate was evaporated under reduced pressure to give a residue. The residue was heated with 50 ml of hexane. The hot hexane was decanted from a tarry residue and cooled to yield a solid precipitate, which was collected by filtration, then dried to give 3.3 g of solid, m.p. 97°-103° C. Concentration of the mother liquor provided a second fraction of solid weighing 0.8 g, m.p. 96°-103° C. Nmr spectra of the two fractions indicated the solids were each trans-3-[2-chloro-3,3,3-trifluoropropenyl]-2,2-dimethylcyclopropanecarboxylic acid. The mother liquor was evaporated to a residue. The residue was taken up in 50 ml of hexane and the solution cooled in a freezer for 18 hours. A solid precipitate was collected by filtration and dried to give 4.3 g of a solid, m.p. 64°-74° C. An nmr spectrum indicated the solid was a 50/50 mixture of cis and trans isomers of 3-[2-chloro-3,3,3-trifluoropropenyl]-2,2-dimethylcyclopropanecarboxylic acid.

Additional free acids of formula V, prepared in accordance with Example 4, are set forth as Examples 4.1 through 4.7 of Table III.

EXAMPLE 5

SYNTHESIS OF TRANS-3-[2-CHLORO-3,3,3-TRIFLUORO-PROPENYL]-2,2-DIMETHYLCYCLO-PROPANECARBONYL CHLORIDE

To a stirred solution of 4.1 g (0.0173 mole) of trans-3-[2-chloro-3,3,3-trifluoropropenyl]-2,2-dimethylcyclopropanecarboxylic acid in 40 ml of toluene at ambient temperature was added 1.7 g (0.022 mole) of pyridine, then 2.6 g (0.022 mole) of thionyl chloride in 25 ml of toluene. Upon complete addition the reaction mixture was stirred at ambient temperature for 17 hours. The reaction mixture was filtered through diatomaceous earth, and the filtrate was evaporated under reduced pressure to give 3.8 g of trans-3-[2-chloro-3,3,3-trifluoropropenyl]-2,2-dimethylcyclopropanecarbonyl chloride. The ir spectrum was consistent with the assigned structure.

Additional acid chlorides of Formula V, prepared by the method illustrated in Example 5, are set forth as Examples 5.1 through 5.8 in Table III.

EXAMPLE 6

SYNTHESIS OF 5-BENZYL-3-FURYLMETHYL CIS,TRANS-3-[2-CHLORO-3,3,3-TRIFLUORO-PROPENYL]-2,2-DIMETHYLCYCLO-PROPANECARBOXYLATE

To a stirred solution of 5.0 g (0.021 mole) of cis,trans-3-[2-chloro-3,3,3-trifluoropropenyl]-2,2-dimethylcyclopropanecarboxylic acid in 85 ml of toluene at ambient temperature was added 2.74 g (0.023 mole) of thionyl chloride, then 4.4 g (0.055 mole) of pyridine. Upon complete addition the reaction mixture was stirred at ambient temperature for 6 hours. 5-Benzyl-3-furylmethyl alcohol (4.13 g, 0.022 mole) in 100 ml toluene was then added to the reaction mixture, followed by 2.7 ml of pyridine, and the reaction mixture stirred overnight. The reaction mixture was filtered and the filtrate was washed with a saturated solution of sodium bicarbonate, dried, and concentrated to give 5.6 g of a yellow oil which was chromatographed on a column of 60 g of $SiO_2$ eluting with hexane then with a 9:1 mixture of hexane/ether. Two fractions obtained with the hexane/ether eluate contained 5-benzyl-3-furylmethyl cis,-trans-3-[2-chloro-3,3,3-trifluoropropenyl]-2,2-dimethylcyclopropanecarboxylate. One fraction contained 3.7 g of 94% purity, the other 0.9 g of 90% purity. The nmr was consistent with the assigned structure.

Analysis calc'd: C 61.09; H 4.88; Found: C 60.84; H 4.82.

EXAMPLE 7

5-Benzyl-3-furylmethyl cis-3-[2-chloro-3,3,3-trifluoropropenyl]-2,2-dimethylcyclopropanecarboxylate was prepared from the cis carboxylic acid in the manner set forth in Example 6. The nmr spectrum was consistent with the assigned structure.

Analysis calc'd: C 61.09; H 4.88; Found: C 60.98; H 4.80.

In the method aspect of this invention an effective insecticidal amount of the compound is applied to the locus where insect control is desired, i.e., to the insect itself or to the foliage or seeds of agricultural plants. The compounds are useful for the control of household, veterinary, and crop insects and may be applied as technical material or as a formulated product. Typical formulations include compositions of the active ingredient in combination with an agriculturally acceptable carrier or extender, preferably with a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of the active ingredient depending upon the particular agent used, the additives and carriers used, other active ingredients and the desired mode of application. With due consideration of these factors, the active ingredient of a typical formulation may, for example, be suitably present at a concentration of about 0.1% up to about 99.5% by weight of the formulation. An agriculturally acceptable carrier may comprise about 99.5% by weight to as low as about 0.5% by weight of the formulation. Compatible surface-active agents, if employed in the formuation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight.

Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, etc.

In applying these compounds, whether alone or with other agricultural chemicals, an effective insecticidal amount of the active ingredient must be applied. While the application rate will vary widely depending on the choice of compound, the formulation and mode of application, the plant species beig protected, and the planting density, a suitable use rate may be in the range of 0.005 to 3 kg./hectare, preferably 0.01 to about 1 kg./hectare.

The compounds of this invention were tested for initial insecticidal activity as described below.

EXAMPLE 8

Initial Contact Activity

The test compound was dissolved in a small amount of acetone, and the acetone solution was dispersed in water containing one drop of isooctylphenyl polyethoxyethanol to make a solution having 1250 ppm (w/w) or 512 ppm (w/w) active ingredient. Aliquots of this solution were diluted with an appropriate amount of water to provide solutions containing various concentrations of active ingredient. Test organisms and techniques were as follows: the activity against Mexican bean beetle (*Epilachna varivestis* Muls.) and southern armyworm (*Spodoptera eridania* [Cram.]) was evaluated by dipping the leaves of pinto bean plants into the test solution or spraying with the test solution and infesting the leaves with the appropriate immature-form insects after the foliage had dried. The activity against the pea aphid (*Acyrthosiphon pisum* [Harris]) was evaluated on broad bean plants whose leaves were dipped or sprayed before infestation with adult aphids. The activity against twospotted spider mites (*Tetranychus urticae* [Koch]) was evaluated on pinto bean plants whose leaves were dipped or sprayed with test solution after infestation with adult mites. The activity against the milkweed bug (*Oncopeltus faciatus* [Dallas]) and the plum curculio (*Conatrachelus nenuphar* [Herbst]) was evaluated by spraying the test solutions into glass dishes or jars containing the adult insects. Following application of the compound and infestation the tests were maintained in a holding room at 80° F. and 50% relative humidity for an exposure period of at least 48 hours. At the end of this time the dead and living insects or mites were counted, and the percent kill was calculated. Results of these tests are summarized in the table below. This table also reports data at 156, 39 and 10 parts per million for the commercial insecticide permethrin, 3-phenoxybenzyl (±) cis,trans-3-(2,2-dichlorovinyl)-2,2-dimethylcyclopropane-1-carboxylate. The abbreviations used in the table, MWB, MBB, SAW, PA, SM, PC, are for milkweed bug, Mexican bean beetle, southern armyworm, pea aphid, twospotted spider mite, and plum curculio respectively. The check test was conducted with an untreated sample. The claimed compounds in general exhibit excellent initial activity relative to the reference compound.

| Compound of Example | Conc. (ppm) | INITIAL ACTIVITY Percent Kill | | | | | |
|---|---|---|---|---|---|---|---|
| | | MWB | MBB | SAW | PA | SM | PC |
| 6 | 64 | — | 100 | 100 | 100 | 0 | — |
| 7 | 64 | — | 100 | 100 | 100 | 0 | — |
| permethrin | 156 | 71 | — | — | 94 | 36 | 100 |
| | 39 | 30 | 100 | 100 | 93 | — | 33 |
| | 10 | 10 | 75 | 100 | 54 | — | 15 |
| Check | — | 0 | 0 | 5 | 10 | 0 | 0 |

EXAMPLE 9

Topical Application Test

The compounds of this invention were tested for insecticidal activity by applying to the insect appropriate amounts of a toxicant solution containing 5 mg/l of toxicant in acetone. The tests were read twenty-four hours after application of the toxicant solution and the percent kill determined. The commercial insecticide permethrin, 3-phenoxybenzyl (±) cis-trans-3-(2,2-dichlorovinyl)-2,2-dimethylcyclopropanecarboxylate, was used as the standard for comparison. Relative potency, based on a value of 1.0 for permethrin was determined by comparing the $LD_{50}$ for the test compound with that for the standard. The insects employed include southern armyworm (*Spodoptera eridania* [Cram.]), cabbage looper (*Trichopusia ni* [Hubner]), beet armyworm (*Spodoptera exigua* [Hubner]), and corn earworm (*Heliothis zea* [Boddie]), Mexican bean beetle (*Epilachna varivestis* Muls.) and milkweed bug (*Oncopeltus faciatus* [Dallas]).

The results, shown in the table below, demonstrate the surprising insecticidal efficacy of the preferred compounds of this invention when compared with permethrin and with the compounds designated A and B. Compound A is 3-phenoxybenzyl cis-3-[2-chloro-3,3,3-trifluoropropenyl]-2,2-dimethylcyclopropanecarboxylate. Compound B is 5-benzyl-3-furymethyl cis-2,2-dichlorovinyl-2,2-dimethylcyclopropanecarboxylate, claimed in U.S. Pat. No. 4,024,163, supra. The abbreviations used in the table, SAW, CL, BAW, CEW, MBB, and MWB, are for southern armyworm, cabbage looper, beet armyworm, corn earworm, Mexican bean beetle, and milkweed bug respectively.

| Compound of Example | Relative Potency Against | | | | | |
|---|---|---|---|---|---|---|
| | SAW | CL | BAW | CEW | MBB | MWB |
| permethrin | 1.0 | 1.0 | 1.0 | 1.0 | 1.0 | 1.0 |
| 6 | 6.4 | 8.2 | 7.9 | | 3.8 | 55.7 |
| 7 | 12.2 | 11.8 | 24.1 | 7.8 | 7.9 | 67.6 |
| A | 2.3–2.6 | 2.1–2.7 | 1.9–2.8 | 1.5–1.8 | 7.1 | 2.4 |
| B | 7 | 5 | 4 | — | 2 | 44 |

TABLE I

| Example | X | Y | Z | R |
|---|---|---|---|---|
| 1.1[a] | Br | $CF_3$ | Br | $OCH_3$ |
| 1.2[a] | Cl | $CF_3$ | F | $OCH_3$ |
| 1.3[a] | Cl | $CF_3$ | H | $OCH_3$ |
| 1.4[a] | Cl | $CF_2Cl$ | Cl | $OCH_3$ |
| 1.5[a] | Cl | $CF_2Cl$ | F | $OCH_3$ |
| 1.6[a] | Cl | $CFCl_2$ | F | $OCH_3$ |
| 1.7[a] | Cl | $CF_2CF_2Cl$ | Cl | $OCH_3$ |
| 1.8[b] | Cl | $C_2F_5$ | Cl | $OCH_3$ |

[a] = Boiling points (°C./mmHg): 1.1: 63/0.08; 1.2: 71/0.09; 1.3: 112°–115°/7; 1.4: 95–106/0.1–0.125; 1.5: 58–60/0.005; 1.6: 103/0.2–0.3; 1.7: 98–102/0.05.
[b] = Structure confirmed by nmr.

TABLE II

| Example | X | Y | Z | R |
|---|---|---|---|---|
| 2.1[a] | Br | $CF_3$ | Br | $OCH_3$ |
| 2.2 | Cl | $CF_3$ | F | $OCH_3$ |
| 2.3[b] | Cl | $CF_3$ | H | $OCH_3$ |
| 2.4 | Cl | $CF_2Cl$ | Cl | $OCH_3$ |
| 2.5[a] | Cl | $CF_2Cl$ | F | $OCH_3$ |
| 2.6 | Cl | $CFCl_2$ | F | $OCH_3$ |

TABLE II-continued

| Example | X | Y | Z | R |
|---|---|---|---|---|
| 2.7[b] | Cl | $CF_2CF_2Cl$ | Cl | $OCH_3$ |

[a] = Boiling points: (°C./mmHg): 2.1: 100–113°/0.09–0.1; 2.5: 45–47°/0.02
[b] = Structure confirmed by nmr.

TABLE III

| Example | Y | Z | R | Isomer |
|---|---|---|---|---|
| 3.1[b] | $CF_3$ | Br | $OCH_3$ | c/t |
| 3.2[b] | $CF_3$ | F | $OCH_3$ | c/t |
| 3.3 | $CF_3$ | H | $OCH_3$ | c/t |
| 3.4[b] | $CF_2Cl$ | Cl | $OCH_3$ | c/t |
| 3.5[b] | $CF_2Cl$ | F | $OCH_3$ | c/t |
| 3.6[b] | $CFCl_2$ | F | $OCH_3$ | c/t |
| 3.7[b] | $CF_2CF_2Cl$ | Cl | $OCH_3$ | c/t |
| 3.8[b] | $C_2F_5$ | Cl | $OCH_3$ | c/t |
| 4.1[c] | $CF_3$ | Br | OH | c/t |
| 4.2[d] | $CF_3$ | F | OH | c/t |
| 4.3[a] | $CF_3$ | H | OH | c/t |
| 4.4[a] | $CF_2Cl$ | Cl | OH | c/t |
| 4.5[c] | $CF_2Cl$ | F | OH | c |
| 4.6[c] | $CF_2CF_2Cl$ | Cl | OH | c/t |
| 4.7 | $C_2H_5$ | Cl | OH | c/t |
| 5.1[e] | $CF_3$ | Br | Cl | c/t |
| 5.2[e] | $CF_3$ | F | Cl | c/t |
| 5.3[f] | $CF_3$ | H | Cl | c/t |
| 5.4[e] | $CF_2Cl$ | Cl | Cl | c/t |
| 5.5[d,e] | $CF_2Cl$ | F | Cl | c |
| 5.6[d,e] | $CF_2CF_2Cl$ | Cl | Cl | c/t,Z |
| 5.7[b] | $C_2H_5$ | Cl | Cl | c/t,Z |
| 5.8[d,e] | $CF_3$ | Cl | Cl | c/t,E,Z |

[a] NMR spectrum consistent with assigned structure.
[b] Boiling points (°C./mm Hg): 3.1: 44–47°/0.07–0.08; 3.2: 71°/29; 3.4: 84–88°/1.-25–1.4; 3.5: 90–92°/11; 3.6: 60–71°/0.08; 3.7: 59–65°/0.07; 3.9: 98–110°/7; 5.7: 42–51°/0.1;
[c] Melting points (°C.): 4.1: 110–116°; 4.5: 80–87°; 4.6: 67–69°
[d] = Structure confirmed by IR spectra
[e] = Liquid, not isolated
[f] = Semi-solid, not isolated

I claim:
1. An insecticidal compound of the formula

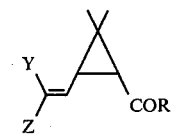

wherein one of Y and Z is a perhaloalkyl group having 1 to 4 carbon atoms and the other is hydrogen, halogen, or lower alkyl; R is $-OR^1$ wherein $R^1$ is represented by the formula

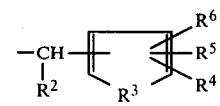

in which $R^2$ is hydrogen, lower alkyl, ethynyl, cyano, or trihalomethyl; $R^3$ is a divalent oxygen; $R^4$ is benzyl which may be substituted with one to three substituents selected from halogen or lower alkyl; $R^5$ and $R^6$ are independently hydrogen, lower alkyl, or halogen.

2. The insecticidal compound of claim 1 in which the perhaloalkyl group has 1-2 carbon atoms.

3. The compound of claim 2 wherein one of Y and Z is trifluoromethyl and the other is halogen.

4. The compound of claim 1, 2 or 3 wherein $R^1$ is represented by the formula

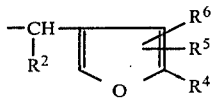

wherein $R^2$, $R^5$ and $R^6$ are each hydrogen.

5. The compound of claim 1, in which the vinyl and carboxy groups at positions 1 and 3 of the cyclopropane ring are of cis or trans or cis,trans configuration with respect to each other.

6. 5-Benzyl-3-furylmethyl 3-[2-chloro-3,3,3-trifluoropropenyl]-2,2-dimethylcyclopropanecarboxylate.

7. An insecticidal compositon comprising an insecticidal amount of the compound of claims 1, 3, 4 or 6 in admixture with a compatible agriculturally acceptable carrier.

8. A method for insect control which comprises applying to the situs where control is desired an insecticidally effective amount of the compound of claims 1, 3, 4 or 6.

9. A method for insect control which comprises applying to the situs where control is desired an insecticidally effective amount of the composition of claim 7.

* * * * *

UNITED STATES PATENT AND TRADEMARK OFFICE
CERTIFICATE OF CORRECTION

PATENT NO. : 4,235,927
DATED : 25 November 1980
INVENTOR(S) : John F. Engel

It is certified that error appears in the above-identified patent and that said Letters Patent are hereby corrected as shown below:

Column 5, line 35, "[2-chloro-3,3-trifluoropropenyl]" should read --[2-chloro-3,3,3-trifluoropropenyl--.
Column 7, line 65, "beig" should read --being--.
Colume 9, line 9, "Trichopusia" should read --Trichoplusia--. Column 10, in Table III, line 33, "$C_2H_5$" should read --$C_2F_5$--; Column 10, in Table III, line 38, "$C_2H_5$" should read --$C_2F_5$--.

Signed and Sealed this

Twelfth Day of October 1982

[SEAL]

Attest:

GERALD J. MOSSINGHOFF

Attesting Officer    Commissioner of Patents and Trademarks